US012367399B2

(12) United States Patent
Stroh et al.

(10) Patent No.: US 12,367,399 B2
(45) Date of Patent: Jul. 22, 2025

(54) TEMPORALLY DYNAMIC LOCATION-BASED PREDICTIVE DATA ANALYSIS

(71) Applicant: UnitedHealth Group, Incorporated, Minnetonka, MN (US)

(72) Inventors: Alison R. Stroh, Minnetonka, MN (US); Mario M. Suarez, Ashburn, VA (US); Stephen R. Dion, Reading, MA (US); Jordan R. DiPascal, Knightdale, NC (US); Derek J. Syverson, Minneapolis, MN (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 1005 days.

(21) Appl. No.: 17/335,260

(22) Filed: Jun. 1, 2021

(65) Prior Publication Data

US 2022/0101150 A1 Mar. 31, 2022

Related U.S. Application Data

(60) Provisional application No. 63/085,226, filed on Sep. 30, 2020.

(51) Int. Cl.
*G06N 5/02* (2023.01)
*G06N 20/00* (2019.01)

(52) U.S. Cl.
CPC ............... *G06N 5/02* (2013.01); *G06N 20/00* (2019.01)

(58) Field of Classification Search
CPC .......... G06N 5/02; G06N 20/00; G06N 3/044; G16H 50/20; G16H 50/80
See application file for complete search history.

(56) References Cited

U.S. PATENT DOCUMENTS

| 9,746,985 | B1 | 8/2017 | Humayun et al. |
| 10,418,133 | B2 | 9/2019 | Arora |
| 11,127,506 | B1* | 9/2021 | Jain ........................ H04W 4/021 |
| 2009/0082997 | A1 | 3/2009 | Tokman et al. |
| 2014/0167917 | A2 | 6/2014 | Wallace et al. |
| 2015/0095333 | A1* | 4/2015 | Porpora ................... G06F 16/35 |
| | | | 707/754 |

(Continued)

FOREIGN PATENT DOCUMENTS

CN 201993759 U 9/2011

OTHER PUBLICATIONS

"Risk Perception and Compliance with Quarantine During the SARS Outbreak", Cava et al., Journal of Nursing Scholarship, 2005 (Year: 2005).*

(Continued)

*Primary Examiner* — Hope C Sheffield
(74) *Attorney, Agent, or Firm* — Alston & Bird LLP

(57) ABSTRACT

Various embodiments of the present invention provide methods, apparatus, systems, computing devices, computing entities, and/or the like for performing temporally dynamic location-based predictive data analysis. Certain embodiments of the present invention utilize systems, methods, and computer program products that perform temporally dynamic location-based predictive data analysis by using at least one of cohort generation machine learning models and cohort-based growth forecast machine learning models.

20 Claims, 7 Drawing Sheets

(56) References Cited

U.S. PATENT DOCUMENTS

2019/0252078 A1 8/2019 Schubert et al.
2020/0294680 A1 9/2020 Gupta et al.

OTHER PUBLICATIONS

Alamo, Teodoro et al. "Data-Driven Methods to Monitor, Model, Forecast and Control Covid-19 Pandemic: Leveraging Data Science, Epidemiology and Control Theory," arXiv:2006.01731v2 [q-bio.PE], Jun. 10, 2020, (65 pages).

Cinelli, Matteo et al. "The COVID-19 Social Media Infodemic," Scientific Reports, vol. 10, No. 16598, Oct. 6, 2020, (10 pages), DOI: 10.1038s41598-020-73510-5.

Eikenberry, Steffen E. et al. "To Mask or Not to Mask: Modeling the Potential for Face Mask Use by the General Public to Curtail the COVID-19 Pandemic," Infectious Disease Modelling, Apr. 21, 2020, vol. 5, pp. 293-308, DOI: 10.1016/j.idm.2020.04.001, PMID: 32355904, PMCID: PMC7186508.

Shorman, Jonathan et al. "Kansas Began Requiring Masks, Then Virus Cases Dropped. Weeks Later, 'The Data Is Solid'", The Wichita Eagle, Aug. 16, 2020, (10 pages), [article, online], [Retrieved from the Internet Aug. 16, 2021] <https://www.kansas.com/news/politics-government/article244959870.html>.

Shuja, Junaid et al. "COVID-19 Open Source Data Sets: A Comprehensive Survey," Applied Intelligence, Sep. 21, 20201, vol. 51, pp. 296-1325, DOI: 10.1007/s10489-020-01862-6.

Streiff, Lara. "Models Explore How Disease Dynamics Change When Cultural Behaviors Harmful to Health Spread Like a Pathogen," Standford News, Sep. 8, 2020, (4 pages), [Retrieved from the Internet Aug. 16, 2021] <https://news.stanford.edu/2020/09/08/modeling-behaviors-spread-disease/>.

* cited by examiner

TEMPORALLY DYNAMIC LOCATION-BASED PREDICTIVE DATA ANALYSIS

CROSS-REFERENCES TO RELATED APPLICATION(S)

The present application claims priority to U.S. Provisional Patent Application No. 63/085,226 (filed Sep. 30, 2020), which is incorporated herein by reference in its entirety.

BACKGROUND

Various embodiments of the present invention address technical challenges related to performing predictive data analysis and address the efficiency and reliability shortcomings of existing predictive data analysis solutions.

BRIEF SUMMARY

In general, embodiments of the present invention provide methods, apparatus, systems, computing devices, computing entities, and/or the like for performing temporally dynamic location-based predictive data analysis. Certain embodiments of the present invention utilize systems, methods, and computer program products that perform temporally dynamic location-based predictive data analysis by using at least one of cohort generation machine learning models and cohort-based growth forecast machine learning models.

In accordance with one aspect, a method is provided. In one embodiment, the method comprises: (i) generating, by using a cohort generation machine learning model, a locality cohort for the input locality data object and the input control policy data object, wherein: (a) the locality cohort comprises one or more cohort locality data objects, (b) each cohort locality data object of the one or more cohort locality data objects is associated with: (1) the input control policy data object, (2) a corresponding cohort locality sentiment designation with respect to the input control policy data object, and (3) a corresponding cohort locality adherence designation with respect to the input control policy data object, (c) each corresponding cohort locality sentiment designation corresponds to a corresponding input locality sentiment designation for the input locality data object with respect to the input control policy data object, and (d) each corresponding cohort locality adherence designation corresponds to a corresponding input locality adherence designation for the input locality data object with respect to the input control policy data object; (ii) generating, by using a cohort-based growth forecast machine learning model, an inferred cross-temporal growth prediction for the input locality data object with respect to the input control policy data object with respect to a plurality of policy-indexed temporal units, wherein the cohort-based growth forecast machine learning model is configured to process a ground-truth cross-temporal growth data object for each cohort locality data object of the one or more cohort locality data objects with respect to the plurality of policy-indexed temporal units to generate the inferred cross-temporal growth prediction; and (iii) performing one or more prediction-based actions based at least in part on the inferred cross-temporal growth prediction.

In accordance with another aspect, a computer program product is provided. The computer program product may comprise at least one computer-readable storage medium having computer-readable program code portions stored therein, the computer-readable program code portions comprising executable portions configured to: (i) generate, by using a cohort generation machine learning model, a locality cohort for the input locality data object and the input control policy data object, wherein: (a) the locality cohort comprises one or more cohort locality data objects, (b) each cohort locality data object of the one or more cohort locality data objects is associated with: (1) the input control policy data object, (2) a corresponding cohort locality sentiment designation with respect to the input control policy data object, and (3) a corresponding cohort locality adherence designation with respect to the input control policy data object, (c) each corresponding cohort locality sentiment designation corresponds to a corresponding input locality sentiment designation for the input locality data object with respect to the input control policy data object, and (d) each corresponding cohort locality adherence designation corresponds to a corresponding input locality adherence designation for the input locality data object with respect to the input control policy data object; (ii) generate, by using a cohort-based growth forecast machine learning model, an inferred cross-temporal growth prediction for the input locality data object with respect to the input control policy data object with respect to a plurality of policy-indexed temporal units, wherein the cohort-based growth forecast machine learning model is configured to process a ground-truth cross-temporal growth data object for each cohort locality data object of the one or more cohort locality data objects with respect to the plurality of policy-indexed temporal units to generate the inferred cross-temporal growth prediction; and (iii) perform one or more prediction-based actions based at least in part on the inferred cross-temporal growth prediction.

In accordance with yet another aspect, an apparatus comprising at least one processor and at least one memory including computer program code is provided. In one embodiment, the at least one memory and the computer program code may be configured to, with the processor, cause the apparatus to: (i) generate, by using a cohort generation machine learning model, a locality cohort for the input locality data object and the input control policy data object, wherein: (a) the locality cohort comprises one or more cohort locality data objects, (b) each cohort locality data object of the one or more cohort locality data objects is associated with: (1) the input control policy data object, (2) a corresponding cohort locality sentiment designation with respect to the input control policy data object, and (3) a corresponding cohort locality adherence designation with respect to the input control policy data object, (c) each corresponding cohort locality sentiment designation corresponds to a corresponding input locality sentiment designation for the input locality data object with respect to the input control policy data object, and (d) each corresponding cohort locality adherence designation corresponds to a corresponding input locality adherence designation for the input locality data object with respect to the input control policy data object; (ii) generate, by using a cohort-based growth forecast machine learning model, an inferred cross-temporal growth prediction for the input locality data object with respect to the input control policy data object with respect to a plurality of policy-indexed temporal units, wherein the cohort-based growth forecast machine learning model is configured to process a ground-truth cross-temporal growth data object for each cohort locality data object of the one or more cohort locality data objects with respect to the plurality of policy-indexed temporal units to generate the inferred cross-temporal growth prediction; and (iii) perform one or more prediction-based actions based at least in part on the inferred cross-temporal growth prediction.

BRIEF DESCRIPTION OF THE DRAWINGS

Figure 1:
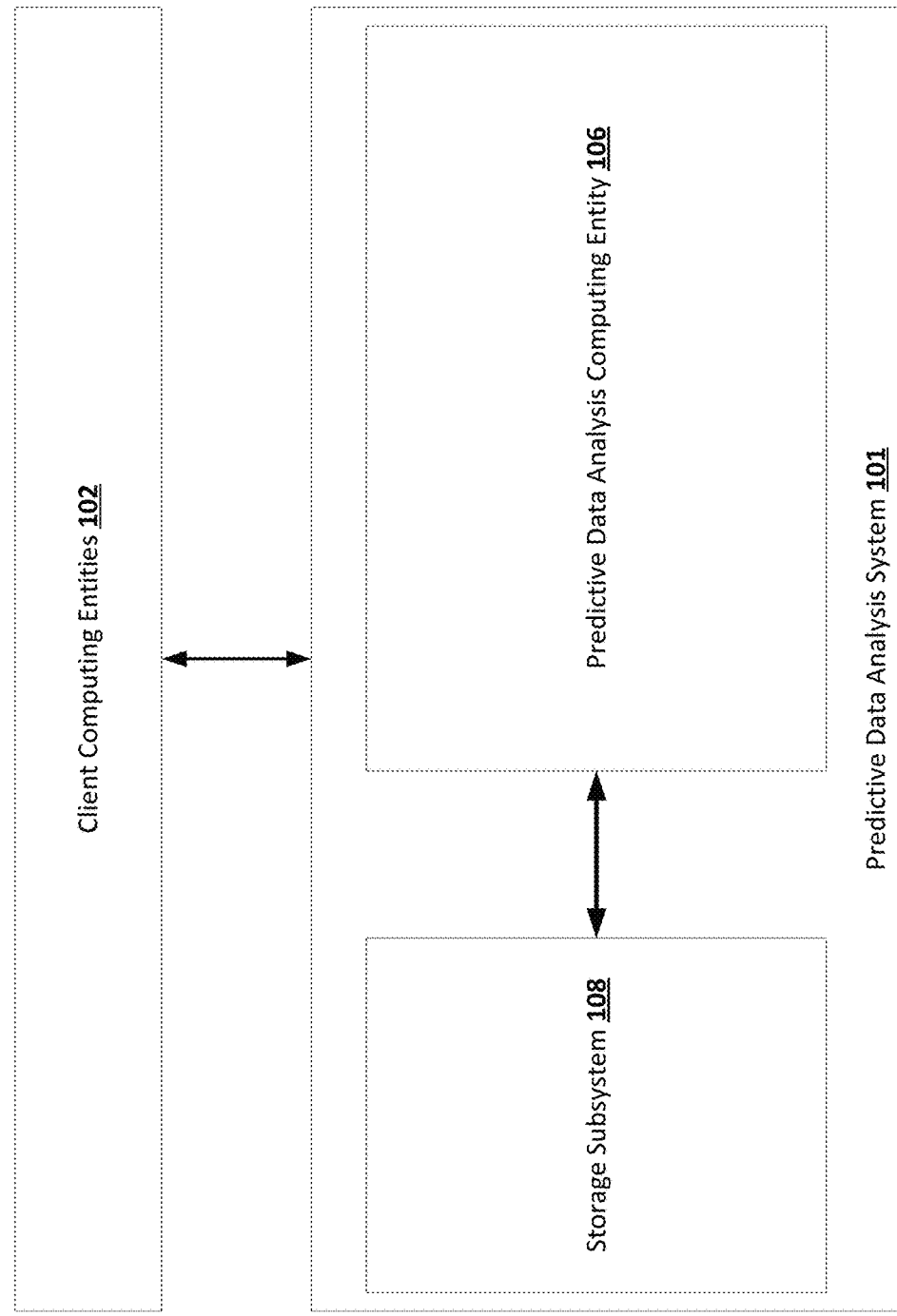

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
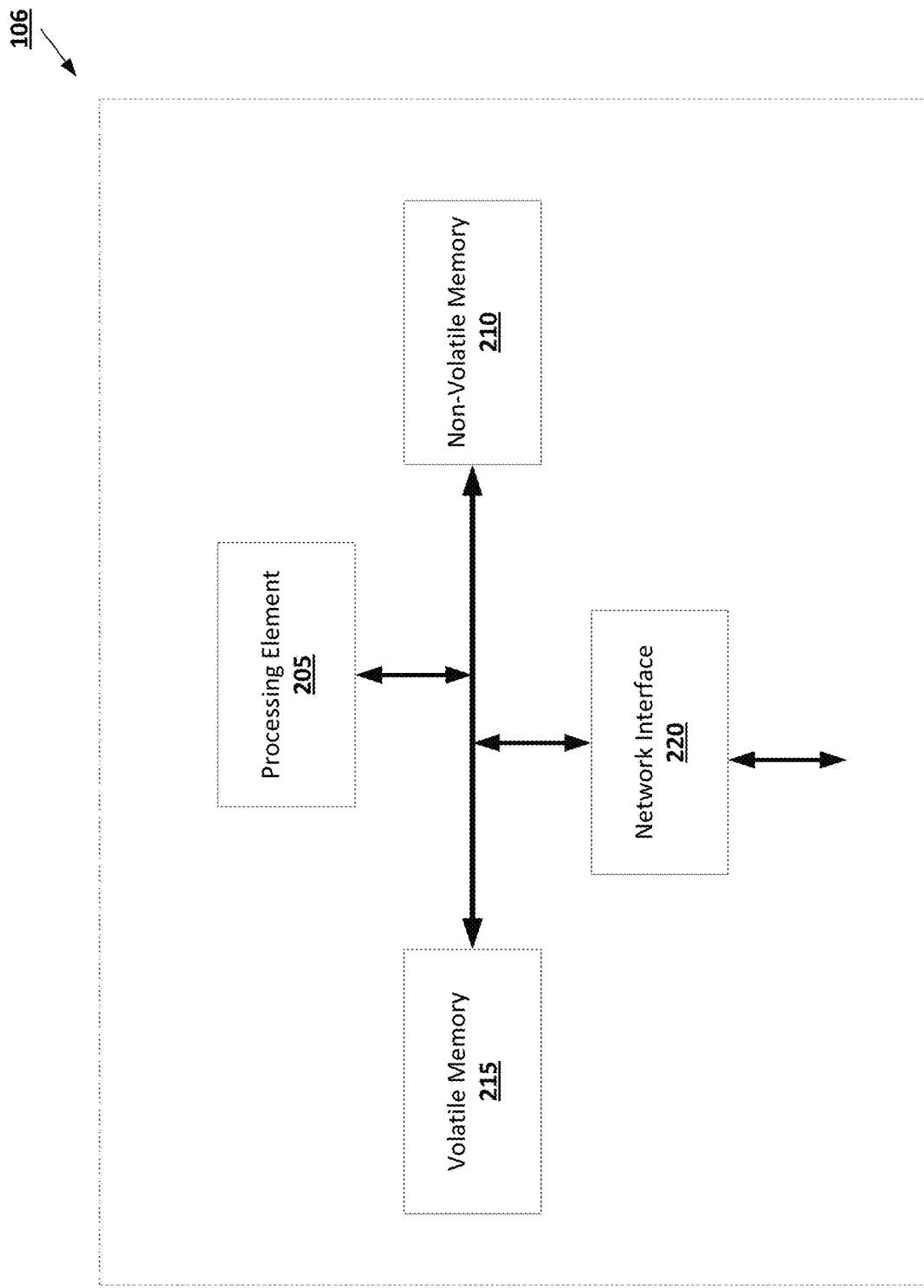

FIG. 2 provides an example predictive data analysis computing entity in accordance with some embodiments discussed herein.

Figure 3:
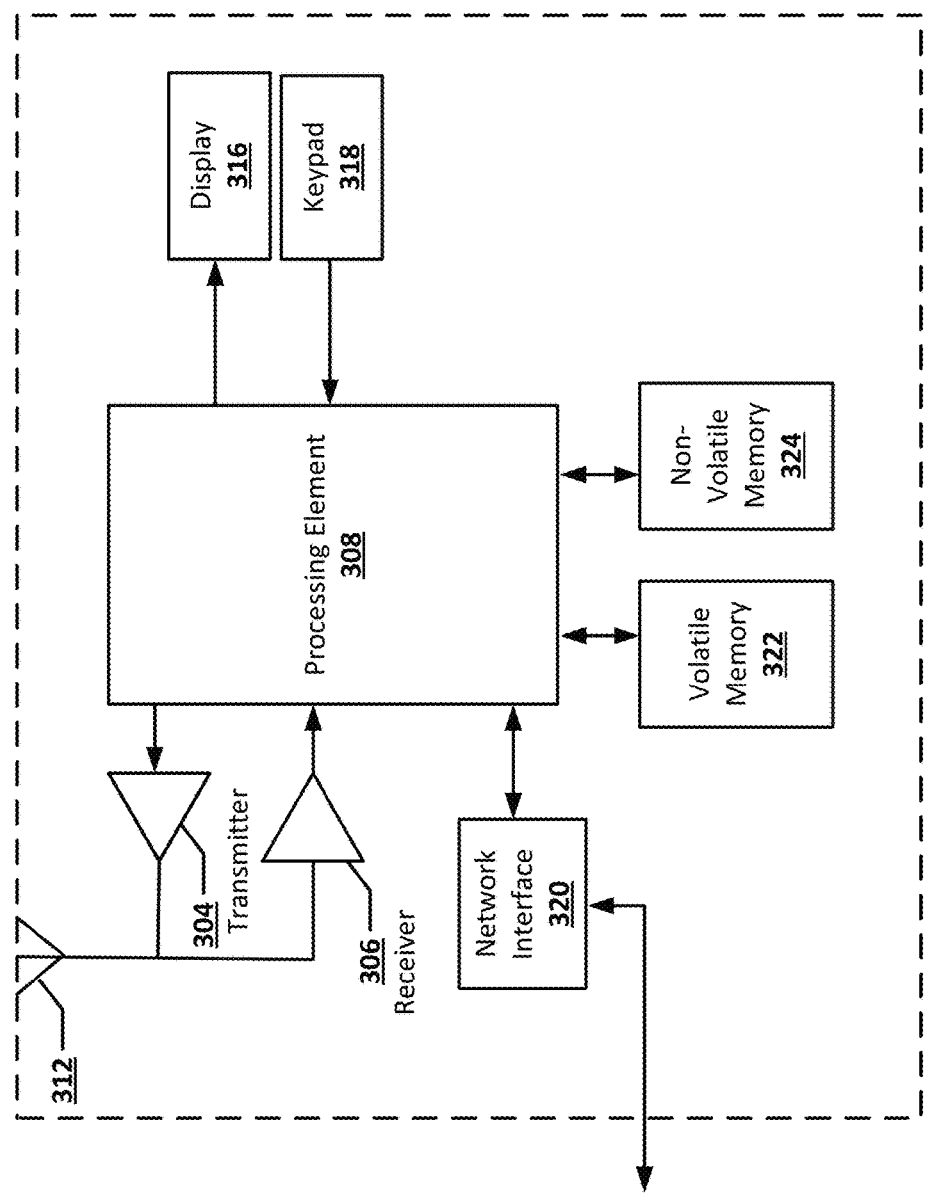

FIG. 3 provides an example client computing entity in accordance with some embodiments discussed herein.

Figure 4:
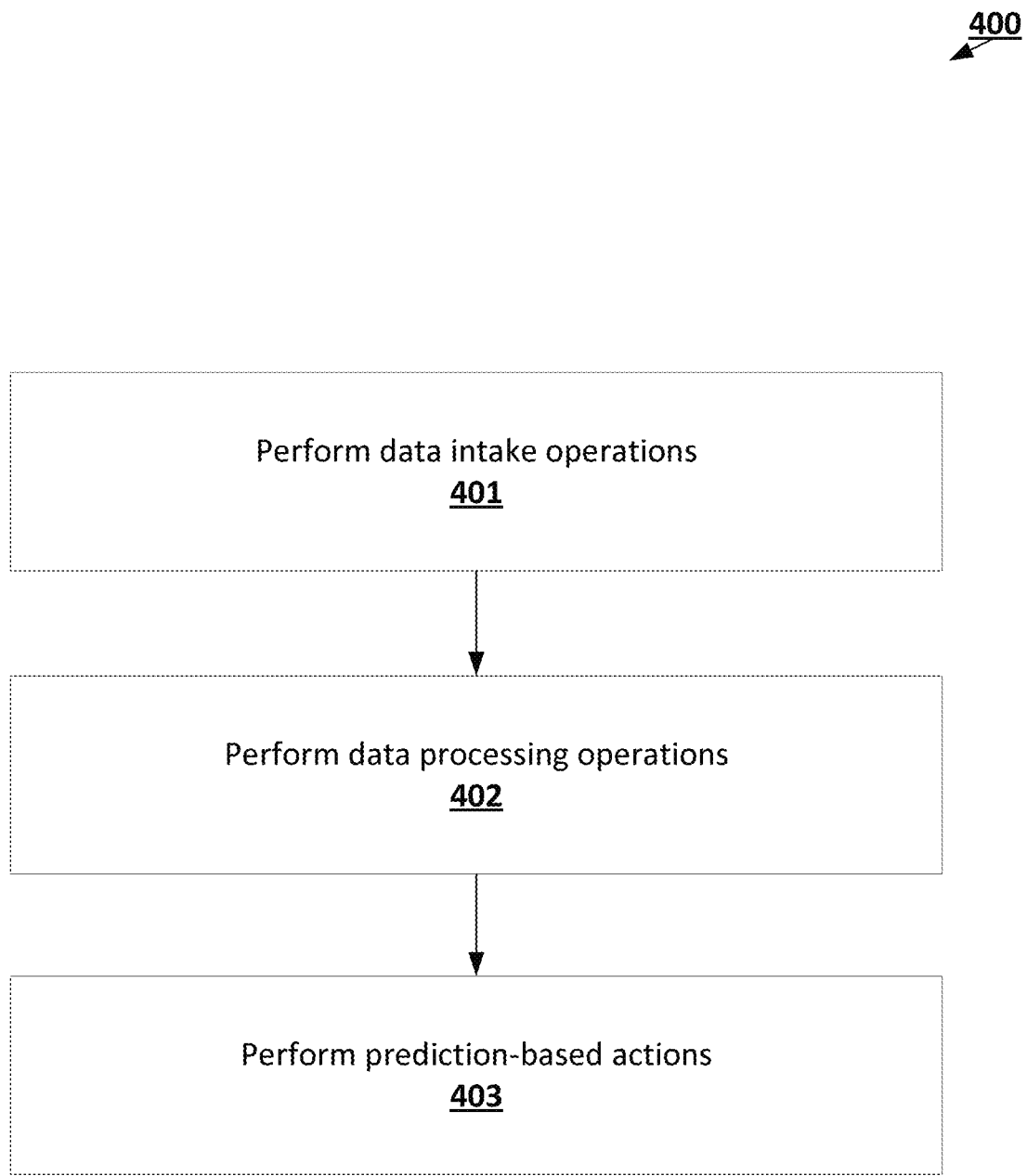

FIG. 4 is a flowchart diagram of an example process for performing temporally dynamic location-based predictive data analysis for an input locality data object given an input control policy data object in accordance with some embodiments discussed herein.

Figure 5:
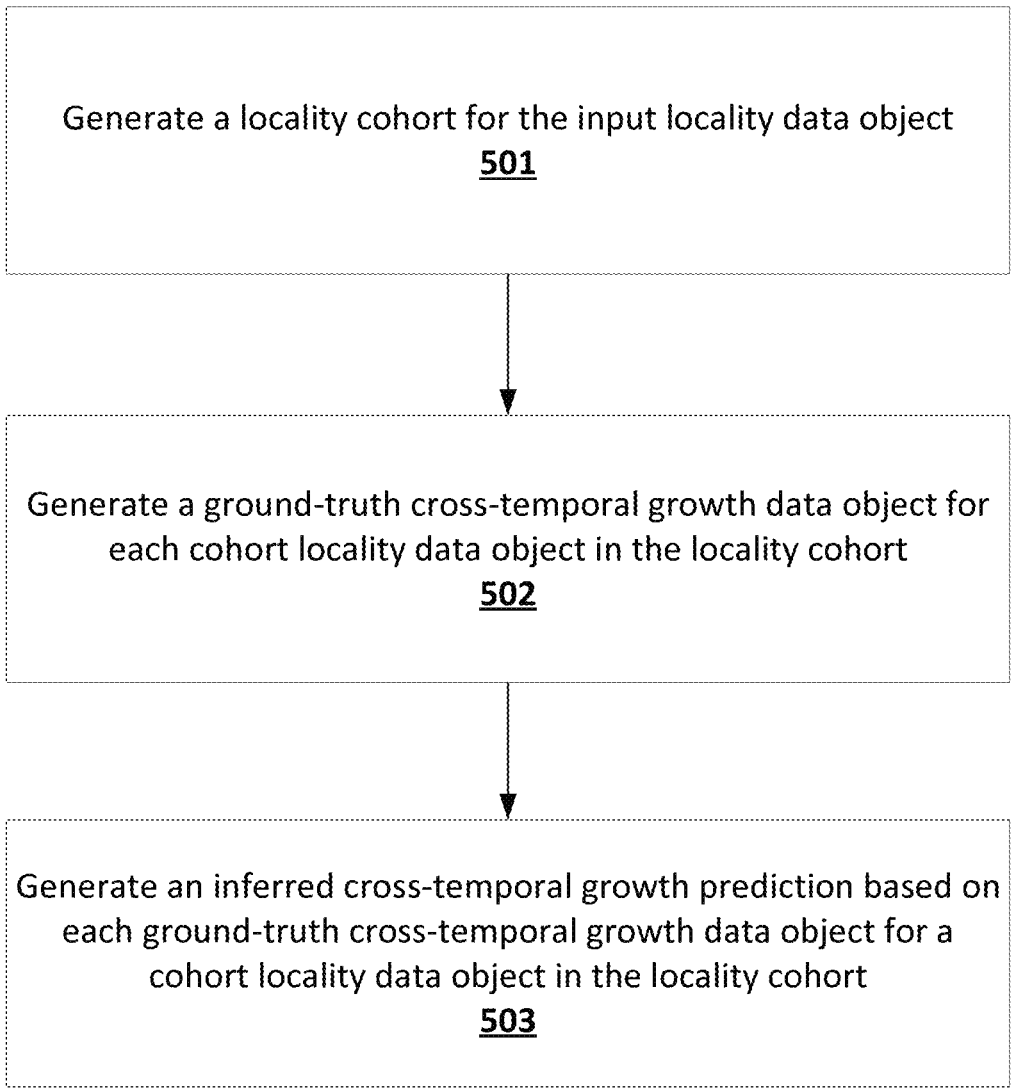

FIG. 5 is a flowchart diagram of an example process for generating an inferred cross-temporal growth prediction for an input locality data object in relation to an input control policy data object in accordance with some embodiments discussed herein.

Figure 6:
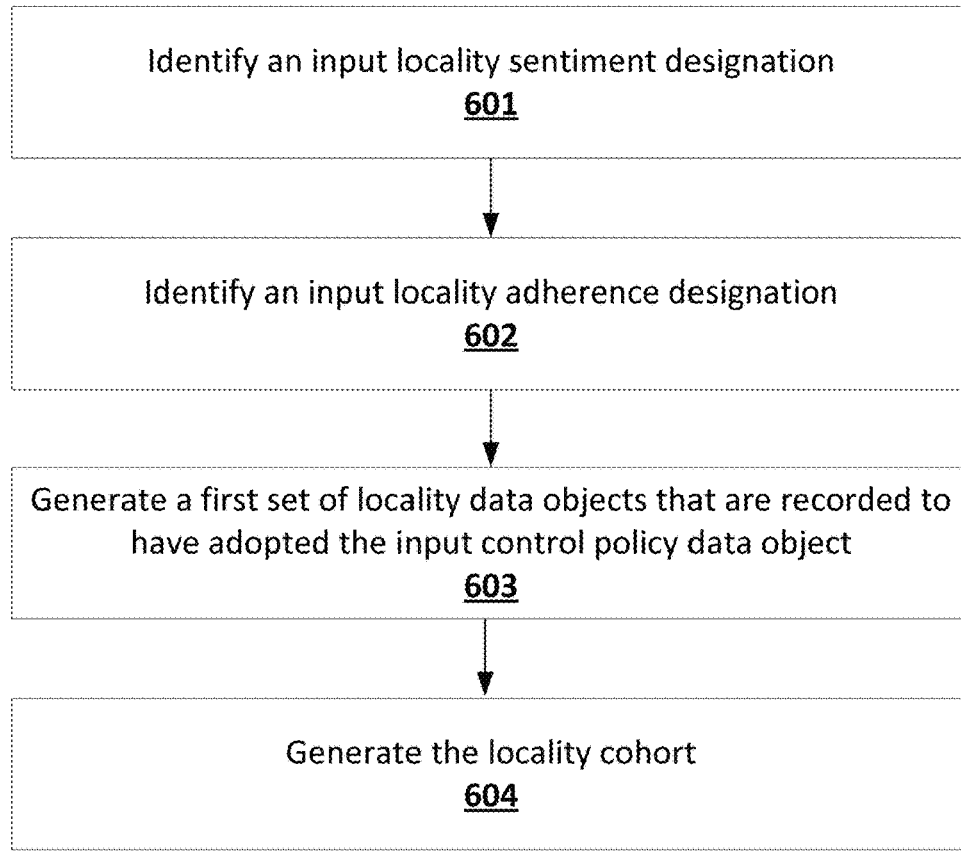

FIG. 6 is a flowchart diagram of an example process generating a locality cohort for an input locality data object and an input control policy data object in accordance with some embodiments discussed herein.

Figure 7:
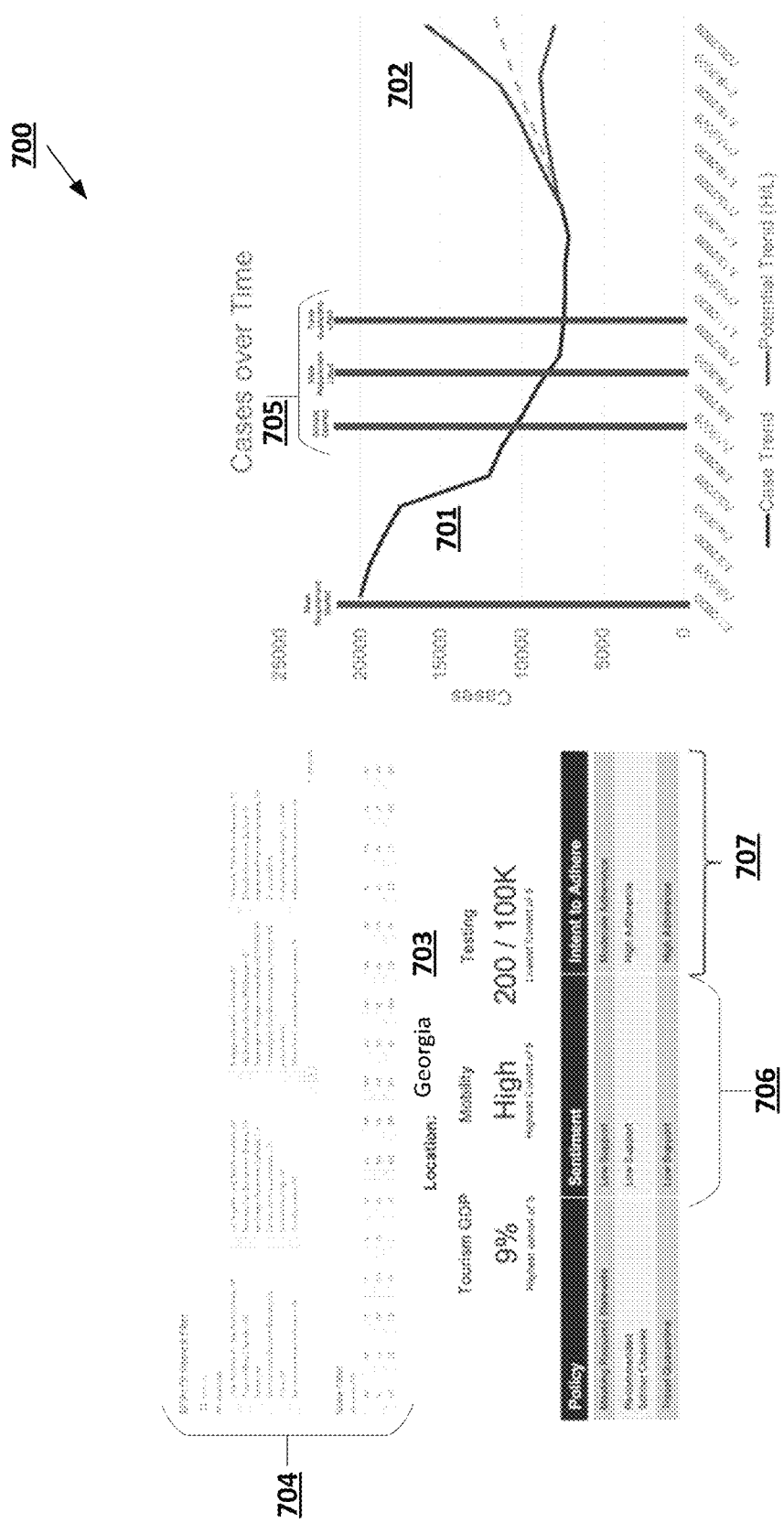

FIG. 7 provides an operational example of a prediction output user interface in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW AND TECHNICAL IMPROVEMENTS

Various embodiments of the present invention address technical challenges related to efficiency of performing cross-temporal location-based predictive data analysis. Various existing location-based predictive data analysis solutions suffer from substantial efficiency challenges resulting from the large number of location data objects that they need to process in order to generate predictive inferences. In contrast, various embodiments of the present invention utilize locality cohorts to reduce the number of cross-temporal predictive data analysis operations that are performed to generate a cross-temporal prediction, thus in turn improving the computational efficiency of performing temporally dynamic location-based predictive data analysis operations that should be performed in order to generate cross-temporal predictions for input locality data objects with respect to input control policy data objects. In doing so, various embodiments of the present invention reduce the computational load of performing cross-temporal location-based predictive data analysis, reduce the amount of storage resources needed to perform cross-temporal location-based predictive data analysis, and make important technical contributions to the field of cross-temporal location-based predictive data analysis.

An exemplary application of various embodiments of the present invention relates to identifying effectiveness of disease control policies based at least in part on cross-location inferences. For example, various embodiments of the present invention: (i) identify disease control policies currently in place, (ii) describe public sentiment with respect to the noted policies, (iii) indicate potential future trends of case counts and infection rates based at least in part on the policies and the public sentiment toward them, and (iv) organize the case count/infection rate data into specific geographies. In doing so, various embodiments of the present invention solve technical problems related to how to evaluate the impact of disease control policies on the trend of disease counts and infection rates.

In some embodiments, various embodiments of the present invention are configured to make predictions about the projected trend of disease growth in a target locality in response to adaptation of a particular disease control policy based at least in part on a projected social sentiment toward the particular disease control policy in the target locality and a projected adherence rate toward the particular disease control policy in the target locality by performing the below operations: identifying a set of related localities in which the particular disease control policy has been adopted in the past, the particular projected social sentiment toward the particular disease control policy exists, and the particular projected adherence rate toward the particular disease control policy exists; for each related locality in the set of related localities, determining a disease trend observation for each day after adaptation of the particular disease control policy; and for each day after adaptation of the particular control policy, determining a projected disease trend for the target locality based at least in part on each disease trend observation for the particular day. In some embodiments, various embodiments of the present invention display a disease trend projection user interface that enables end-users to modify assumptions about particular disease control policies, about adherence rates toward particular disease control policies, and about social sentiments particular disease control policies.

II. DEFINITIONS

The term "input locality data object" may refer to a data entity that is configured to describe a locality (e.g., a spatial unit, a geographic unit, an administrative division unit, and/or the like) with respect to which one or more predictive data analysis operations may be performed. For example, in some embodiments, an input locality data object may describe a geographic unit (e.g., a city, state, province, country, and/or the like) with respect to which one or more predictive data analysis operations may be performed in order to generate a disease spread prediction (e.g., a disease growth rate prediction) for the geographic unit. In some of the noted embodiments, the disease spread prediction for a geographic unit may describe a projected growth rate for a corresponding disease in the geographic unit assuming a particular disease spread control policies are adopted. For example, in some embodiments, a disease spread prediction for a geographic unit may describe a projected growth rate for a corresponding disease in the geographic unit for each day of n days after an assumed adoption of a particular disease spread control policy in the geographic unit with respect to the corresponding disease. An input locality data object is an example of a locality data object, where a locality data object may describe a corresponding locality. A locality data object may be an atomic value or an array of values.

The term "input control policy data object" may refer to a data entity that is configured to describe an event that may be adopted in a locality corresponding to an input locality data object, where the adoption of the event is a condition of the predictive data analysis operations that may be performed with respect to the input locality data object in order to generate a disease spread prediction (e.g., a disease growth rate prediction) for the geographic unit. Examples of input control policy data objects include input control policy data objects that describe mask mandates of various scopes and/or various fine severity magnitudes, lockdown orders of various scopes and/or various fine severity magnitudes, social distancing orders of various scopes and/or various fine severity magnitudes, and/or the like. In some embodiments, each input control policy data object is characterized by a control policy type (e.g., a control policy type that describes that a corresponding control policy is a mask mandate) as well as one or more policy severity magnitude values (e.g., a fine severity magnitude value that describes a fine severity magnitude of a corresponding control policy, a policy severity magnitude value that describes an enforcement scope severity magnitude of a corresponding control policy, and/or the like). In some embodiments, an input control policy data object may describe two or more control policy data objects that may be assumed to be adopted at the same adoption timestamp in relation to an input locality data object for the purposes of performing predictive data analysis operations with respect to the input locality data object and the input control policy data object. The input control policy data object is an example of a control policy data object, where a control policy data object may describe an event such as a control policy that may be adopted by a locality. A control policy data object may be an atomic value or an array of values.

The term "disease-spread-related data object" may refer to a data entity that is configured to describe one or more data fields associated with spread of a particular disease, such as one or more data fields associated with a number of active infection cases for the particular disease for a locality data object at a particular unit of time, one or more data fields associated with a number of reported deaths resulting from the particular disease for a locality data object at a particular unit of time, one or more data fields associated with adoption of control policy data objects associated with a locality data object at a particular unit of time, one or more data fields associated with locality sentiment designations for particular locality data objects with respect to particular control policy data objects, one or more data fields associated with locality adherence designations for particular locality data objects with respect to particular control policy data objects, one or more data fields associated with demographic features for particular locality data objects, and/or the like. For example, in some embodiments, a disease-spread-related data object may describe, for each locality data object of group of locality data objects describing a locality, at least one of the following: (i) one or more infectious disease counts for the locality with respect to a particular disease across a number of temporal units (e.g., a number of days); (ii) one or more disease-induced death counts for the locality with respect to the particular disease across the number of temporal units; (iii) one or more control policy data objects for the locality each describing a control policy adopted by the locality; (iv) for each control policy data object associated with the locality: (a) an adoption timestamp describing a temporal unit (e.g., a day) in which the corresponding control policy is adopted, (b) a locality sentiment designation for the locality data object with respect to the control policy data object, and (c) a locality adherence designation for the locality data object with respect to the control policy data object; and (v) one or more demographic features of the locality (e.g., a population count of the locality, a density measure for the locality, a sprawl measure for the locality, a mobility measure for the locality, and/or the like). Other examples of data that may be described by disease-spread-related data objects include: masking related data (e.g., Masks4all data, etc.), social media data (e.g., Twitter data, etc.), case count data (e.g., Worldometer data, USAFacts data, etc.), lab testing data (e.g. state reported data such as data reported via ca.gov), tourism spending data (e.g., ustravel.org data), state-based gross domestic product (GDP) data (e.g., bea.gov data), mobility data, applicable jurisdiction-based policy anchor points (e.g., retrieved via county or state department of health websites), and other environmental information as applicable (e.g., sentiment information gathered from non-social media sources such as surveys). A disease-spread-related data object may be an atomic value or an array of values.

The term "inferred cross-temporal growth prediction" may refer to a data entity that is configured to describe an inferred prediction about growth of a target condition (e.g., an infection rate of a target disease, a hospitalization rate of a target disease, a death rate resulting from a target disease, and/or the like) across a group of temporal units (e.g., a group of days) and within the locality described by an input locality data object, where the prediction is performed by assuming that a control policy described by an input control policy data object is adopted at a temporal unit (e.g., on a day) described by a corresponding adoption timestamp of the input control policy data object. For example, the inferred cross-temporal growth prediction for an input locality data object in relation to an input control policy data object may describe, for each day of n days after an assumed adoption time of a control policy described by the input control policy data object in a locality described by an input locality data object, a per-day infection growth rate for a target disease. As another example, the inferred cross-temporal growth prediction for an input locality data object in relation to an input control policy data object may describe, for each day of n days after an assumed adoption time of a control policy described by the input control policy data object in a locality described by an input locality data object, a per-day infection rate for a target disease. As yet another example, the inferred cross-temporal growth prediction for an input locality data object in relation to an input control policy data object may describe, for each day of n days after an assumed adoption time of a control policy described by the input control policy data object in a locality described by an input locality data object, a per-day resulting death rate for a target disease. In some embodiments, the inferred cross-temporal growth prediction comprises a group of inferred temporal growth predictions, where an inferred temporal growth prediction describes an inferred prediction about growth of a target condition (e.g., an infection rate of a target disease, a hospitalization rate of a target disease, a death rate resulting from a target disease, and/or the like) at a policy-indexed temporal unit of a group of policy-indexed temporal units. An inferred cross-temporal growth prediction may be an array of inferred temporal growth predictions.

The term "locality cohort" may refer to a data entity that is configured to describe a group of localities described by a group of cohort locality data objects that are deemed to have adopted an input control policy data object and where at least one of (e.g., both of) the following conditions are true of the group of cohort locality data objects: (i) each cohort locality data object is associated with a corresponding cohort locality sentiment designation with respect to the input control policy data object that corresponds to an input locality sentiment designation for the input locality data object with respect to the input control policy data object, and (ii) each cohort locality data object is associated with a corresponding cohort locality adherence designation with respect to the input control policy data object that corresponds to an input locality adherence designation for the input locality data object with respect to the input control policy data object. For example, the locality cohort for an input locality data object and an input control policy data object may describe a group of localities described by a group of cohort locality data objects that are deemed to have adopted a control policy described by the input control policy data object and where, for each particular locality of the group of localities, a recorded popular sentiment about the control policy in the particular locality corresponds to a recorded popular sentiment about the control policy in the locality described by the input locality data object, and a recorded popular adherence rate about the control policy in the particular locality corresponds to a recorded expected popular adherence rate about the control policy in the locality described by the input locality data object. In some embodiments, the input locality data object is associated with one or more input locality demographic features, each cohort locality data object of the one or more of cohort locality data objects is associated with one or more cohort locality demographic features, and each one or more cohort locality demographic features for a cohort locality data object of the one or more of cohort locality data objects corresponds to the one or more input locality demographic features. A locality cohort may be an array of locality data objects.

The term "cohort generation machine learning model" may refer to a data entity that is configured to describe parameters and/or hyper-parameters (e.g., defined operations) of a model that is configured to process at least one of (e.g., both of) an input locality sentiment designation for the input locality data object with respect to the input control policy data object and an input locality adherence designation for the input locality data object with respect to the input control policy data object in order to generate a locality cohort for the input locality data object and the input control policy data object that includes one or more cohort locality data objects. For example, the cohort machine learning model may be configured to perform the following operations: (i) identifying an input locality sentiment designation for an input locality data object with respect to an input control policy data object and an input locality adherence designation for the input locality data object with respect to the input control policy data object, (ii) generating a first set of locality data objects that are recorded to have adopted the input control policy data object, (iii) generating a second set of locality data objects including each locality data object in the first set of locality data objects that has a locality sentiment designation that corresponds to the input locality sentiment designation and has a locality adherence designation that corresponds to the input locality sentiment designation, and (iv) generating the locality cohort based at least in part on the set of locality data objects. In some embodiments, the cohort machine learning model is a clustering machine learning model (e.g., a k-nearest-neighbor-based clustering machine learning model), such as a clustering machine learning model that is configured to generate the locality cohort based at least in part on processing a mapping of a set of locality cohort data objects to a multi-dimensional mapping space, where the multi-dimensional mapping space is associated with a group of mapping dimensions including a mapping dimension associated with a set of locality sentiment designations and a mapping dimension associated with a set of locality adherence designations.

The term "locality sentiment designation" may refer to a data entity that is configured to describe a recorded popular sentiment toward an event (e.g., a control policy) described by a corresponding control policy data object. For example, the locality sentiment designation may describe a recorded approval rating of a corresponding control policy in a corresponding locality. In some embodiments, the locality sentiment designation for an input locality data object with respect to an input control policy data object is referred to as an input locality sentiment designation, while the locality sentiment designation for a cohort locality data object in a locality cohort with respect to an input control policy data object is referred to as a cohort locality sentiment designation.

The term "locality adherence designation" may refer to a data entity that is configured to describe a recorded/expected popular adherence behavior toward an event (e.g., a control policy) described by a corresponding control policy data object. For example, the locality adherence designation may describe a recorded/expected adherence rating for a corresponding control policy in a corresponding locality. In some embodiments, the locality adherence designation for an input locality data object with respect to an input control policy data object is referred to as an input locality adherence designation, while the locality adherence designation for a cohort locality data object in a locality cohort with respect to an input control policy data object is referred to as a cohort locality adherence designation.

The term "ground-truth cross-temporal growth data object" may refer to a data entity that is configured to describe a recorded property related to growth (e.g., an infection count, an infection rate, a hospitalization count, a hospitalization rate, a death count, a death rate, and/or the like) of a target disease within a corresponding locality data object during a group of policy-indexed temporal units after adoption of a corresponding control policy data object by the corresponding locality data object. In some embodiments, the ground-truth cross-temporal growth data objects includes a set of ground-truth cross-temporal growth feature values each describing a recorded property related to growth of a target disease within a corresponding locality data object during a policy-indexed temporal unit of a group of policy-indexed temporal units. For example, a ground-truth cross-temporal growth data object may describe, for each day of n days after adoption of a control policy data object by a locality data object, an infection rate of a target disease within the locality data object (where n may be defined by a hyper-parameter of a corresponding predictive data analysis system).

The term "policy-indexed temporal unit" may refer to a data entity that is configured to describe a unit of time (e.g., a day) that is defined based at least in part on unit-of-time separation in reference to a unit of time associated with an adaption timestamp of a control policy data object. Examples of policy-indexed temporal units include a set of policy-indexed temporal units that each corresponds to one of n days after a day associated with an adaption timestamp of a control policy data object.

The term "cohort-based growth forecast machine learning model" may refer to a data entity that is configured to describe parameters and/or hyper-parameters (e.g., defined operations) of a model that is configured to process a ground-truth cross-temporal growth data object for each cohort locality data object of the one or more cohort locality data objects with respect to the group of policy-indexed temporal units to generate the inferred cross-temporal growth prediction. The cohort-based growth forecast machine learning model may be a model that is configured to process a ground-truth cross-temporal growth data object for each cohort locality data object the one or more cohort locality data objects for an input locality data object with respect to a group of policy-indexed temporal units to generate the inferred cross-temporal growth prediction for the input control policy data object. In some embodiments, the cohort-based growth forecast machine learning model is configured to: (i) for each policy-indexed temporal unit of a group of policy-indexed temporal units, process each ground-truth cross-temporal growth data object of the plurality of ground-truth cross-temporal predictions for a cohort locality data object of the one or more cohort locality data objects that is associated with the policy-indexed temporal unit using the cohort-based growth forecast machine learning model to generate the inferred temporal growth prediction of a group of inferred temporal growth predictions that is associated with the policy-indexed temporal unit; and (ii) determine the inferred cross-temporal growth prediction based at least in part on each inferred temporal growth prediction for a policy-indexed temporal unit of the plurality of policy-indexed temporal units. In some embodiments, the cohort-based growth forecast machine learning model is configured to: (i) for each input policy-indexed temporal unit of a group of policy-indexed temporal units: (a) identify a predecessor subset for the input policy-indexed temporal unit that comprises the input policy-indexed temporal unit and each policy-indexed temporal unit of the plurality of policy-indexed temporal unit that temporally precedes the input policy-indexed temporal unit, and (b) process each ground-truth cross-temporal growth data object of the group of ground-truth cross-temporal predictions for a cohort locality data object of the one or more cohort locality data objects that is in the predecessor subset for the input policy-indexed temporal unit using the cohort-based growth forecast machine learning model to generate the inferred temporal growth prediction of the group of inferred temporal growth predictions that is associated with the input policy-indexed temporal unit; and (ii) determine the inferred cross-temporal growth prediction based at least in part on each inferred temporal growth prediction for a policy-indexed temporal unit of the group of policy-indexed temporal units. In some embodiments, the cohort-based growth forecast machine learning model is a sequential processing machine learning model (e.g., a recurrent neural network machine learning model, such as a Long Short Term Memory (LSTM) machine learning model).

The term "prediction output user interface data object" may refer to a data entity that is configured to describe a prediction output user interface, where the prediction output user interface is configured to: (a) enable updating the input locality data object from a plurality of candidate input locality data objects comprising the input locality data object and the one or more cohort locality data objects, and (b) describe a historical growth trend for the input locality data object and a projected (i.e., predicted future) growth trend for the input locality data object using a graph-based user interface element. In some embodiments, the projected growth trend is determined based at least in part on the inferred cross-temporal growth prediction for the input locality data object. In some embodiments, the prediction output user interface is configured to enable updating the input control policy data object. In some embodiments, the prediction output user interface is configured to enable updating the input locality sentiment designation. In some embodiments, the prediction output user interface is configured to enable updating the input locality adherence designation. In some embodiments, performing the one or more prediction-based actions further comprises providing the prediction output user interface data object to a client computing entity. In some embodiments, the prediction output user interface is configured to enable end-users of the client computing entity to modify assumptions about particular disease control policies, about adherence rates toward particular disease control policies, and about social sentiments toward particular disease control policies.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing predictive data analysis. The architecture 100 includes a predictive data analysis system 101 configured to receive predictive data analysis requests from client computing entities 102, process the predictive data analysis requests to generate predictions, provide the generated predictions to the client computing entities 102, and automatically perform prediction-based actions based at least in part on the generated predictions. An example of a prediction-based action that can be performed using the predictive data analysis system 101 is a request for generating a predictive output user interface that depict one or more outputs of one or more temporally dynamic location-based predictive data analysis operations for an input locality data object, as further described below.

In some embodiments, predictive data analysis system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more client computing entities 102, process the predictive data analysis requests to generate predictions corresponding to the predictive data analysis requests, provide the generated predictions to the client computing entities 102, and automatically perform prediction-based actions based at least in part on the generated predictions.

The storage subsystem 108 may be configured to store input data used by the predictive data analysis computing entity 106 to perform predictive data analysis as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205.

Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

Exemplary Client Computing Entity

FIG. 3 provides an illustrative schematic representative of an client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the predictive data analysis computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the predictive data analysis computing entity 106 and/or various other computing entities.

In another embodiment, the client computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

Various embodiments of the present invention address technical challenges related to efficiency of performing cross-temporal location-based predictive data analysis. Various existing location-based predictive data analysis solutions suffer from substantial efficiency challenges resulting from the large number of location data objects that they need to process in order to generate predictive inferences. In contrast, various embodiments of the present invention utilize locality cohorts to reduce the number of cross-temporal predictive data analysis operations that are performed to generate a cross-temporal prediction, thus in turn improving the computational efficiency of performing temporally dynamic location-based predictive data analysis operations that should be performed in order to generate cross-temporal predictions for input locality data objects with respect to input control policy data objects. In doing so, various embodiments of the present invention reduce the computational load of performing cross-temporal location-based predictive data analysis, reduce the amount of storage resources needed to perform cross-temporal location-based predictive data analysis, and make important technical contributions to the field of cross-temporal location-based predictive data analysis.

FIG. 4 is a flowchart diagram of an example process 400 for performing temporally dynamic location-based predictive data analysis for an input locality data object given an input control policy data object. Via the various steps/operations of the process 400, the predictive data analysis computing entity 106 can utilize locality cohorts to reduce the number of cross-temporal predictive data analysis operations that are performed to generate a cross-temporal prediction, thus in turn improving the computational efficiency of performing temporally dynamic location-based predictive data analysis operations that should be performed in order to generate cross-temporal predictions for input locality data objects with respect to input control policy data objects.

In general, an input locality data object may describe a locality (e.g., a spatial unit, a geographic unit, an administrative division unit, and/or the like) with respect to which one or more predictive data analysis operations may be performed. For example, in some embodiments, an input locality data object may describe a geographic unit (e.g., a city, state, province, country, and/or the like) with respect to which one or more predictive data analysis operations may be performed in order to generate a disease spread prediction (e.g., a disease growth rate prediction) for the geographic unit. In some of the noted embodiments, the disease spread prediction for a geographic unit may describe a projected growth rate for a corresponding disease in the geographic unit assuming a particular disease spread control policies are adopted. For example, in some embodiments, a disease spread prediction for a geographic unit may describe a projected growth rate for a corresponding disease in the geographic unit for each day of n days after an assumed adoption of a particular disease spread control policy in the geographic unit with respect to the corresponding disease. An input locality data object is an example of a locality data object, where a locality data object may describe a corresponding locality.

An input control policy data object may describe an event that may be adopted in a locality corresponding to an input locality data object, where the adoption of the event is a condition of the predictive data analysis operations that may be performed with respect to the input locality data object in order to generate a disease spread prediction (e.g., a disease growth rate prediction) for the geographic unit. Examples of input control policy data objects include input control policy data objects that describe mask mandates of various scopes and/or various fine severity magnitudes, lockdown orders of various scopes and/or various fine severity magnitudes, social distancing orders of various scopes and/or various fine severity magnitudes, and/or the like. In some embodiments, each input control policy data object is characterized by a control policy type (e.g., a control policy type that describes that a corresponding control policy is a mask mandate) as well as one or more policy severity magnitude values (e.g., a fine severity magnitude value that describes a fine severity magnitude of a corresponding control policy, a policy severity magnitude value that describes an enforcement scope severity magnitude of a corresponding control policy, and/or the like). In some embodiments, an input control policy data object may describe two or more control policy data objects that may be assumed to be adopted at the same adoption timestamp in relation to an input locality data object for the purposes of performing predictive data analysis operations with respect to the input locality data object and the input control policy data object. The input control policy data object is an example of a control policy data object, where a control policy data object may describe an event such as a control policy that may be adopted by a locality.

As described above, the process 400 may be utilized to perform temporally dynamic location-based predictive data analysis for an input locality data object given an input control policy data object. The process 400 begins at step/operation 401 when the predictive data analysis computing entity 106 performs one or more data intake operations to generate a group of disease-spread-related data objects. In some embodiments, performing the data intake operations includes: (i) intaking external public data into the predictive data analysis system 101 (e.g., determining when external data has been updated, pulling in data updates from external sources, pushing notification of data updates to interested parties, and/or the like), and (ii) cleansing of intake data for use in data processing (e.g., cleaning county/Federal Information Processing Standard Publication (FIPS) data to standardize the intake data, joining county-based data into an internal master geography dataset, standardizing formats for dates associated with data fields, and/or the like).

A disease-spread-related data object may describe one or more data fields associated with spread of a particular disease, such as one or more data fields associated with a number of active infection cases for the particular disease for a locality data object at a particular unit of time, one or more data fields associated with a number of reported deaths resulting from the particular disease for a locality data object at a particular unit of time, one or more data fields associated with adoption of control policy data objects associated with a locality data object at a particular unit of time, one or more data fields associated with locality sentiment designations for particular locality data objects with respect to particular control policy data objects, one or more data fields associated with locality adherence designations for particular locality data objects with respect to particular control policy data objects, one or more data fields associated with demographic features for particular locality data objects, and/or the like. For example, in some embodiments, a disease-spread-related data object may describe, for each locality data object of group of locality data objects describing a locality, at least one of the following: (i) one or more infectious disease counts for the locality with respect to a particular disease across a number of temporal units (e.g., a number of days); (ii) one or more disease-induced death counts for the locality with respect to the particular disease across the number of temporal units; (iii) one or more control policy data objects for the locality each describing a control policy adopted by the locality; (iv) for each control policy data object associated with the locality: (a) an adoption timestamp describing a temporal unit (e.g., a day) in which the corresponding control policy is adopted, (b) a locality sentiment designation for the locality data object with respect to the control policy data object, and (c) a locality adherence designation for the locality data object with respect to the control policy data object; and (v) one or more demographic features of the locality (e.g., a population count of the locality, a density measure for the locality, a sprawl measure for the locality, a mobility measure for the locality, and/or the like). Other examples of data that may be described by disease-spread-related data objects include: masking related data (e.g., Masks4all data, etc.), social media data (e.g., Twitter data, etc.), case count data (e.g., Worldometer data, USAFacts data, etc.), lab testing data (e.g. state reported data such as data reported via ca.gov), tourism spending data (e.g., ustravel.org data), state-based gross domestic product (GDP) data (e.g., bea.gov data), mobility data, applicable jurisdiction-based policy anchor points (e.g., retrieved via county or state department of health websites), and other environmental information as applicable (e.g., sentiment information gathered from non-social media sources such as surveys).

At step/operation 402, the predictive data analysis computing entity 106 performs one or more data processing operations on the group of disease-spread-related data objects to generate an inferred cross-temporal growth prediction for the input locality data object with respect to the input control policy data object. In some embodiments, at step/operation 402, the predictive data analysis computing entity 106 is configured to generate a data repository, which may be a repository of available input data (masking data, social media data, testing data, and case count data); a metric inventory, which may be an inventory of available metrics to calculate cases, positivity rates, and infection rates within a population (e.g. cases of COVID-19 per 100,000 people in a population); and one or more user interfaces that are configured to organize results of data processing operations, such as a user interface for a team to organize results of data processing operations for display to interested groups.

In some embodiments, step/operation 402 includes determining the geographic location of specific cases, determining the geographic location of policies, determining the geographic location of adherence and sentiment data, identifying locations relative to internal mappings, and associating sentiment data and maps with policy decisions. In some embodiments, step/operation 402 includes determining applicable policies for each region, determining dates on which policies came into effect, identifying timeframe of cases relative to when a policy came into effect, and integrating impact of multiple policies and sentiments into scenario-based potential trends with upper and lower confidence intervals. In some embodiments, step/operation 402 includes determining confirmed cases by geography, comparing confirmed cases to population within geographical divisions, calculating cases and infection rates on given dates, and calculating potential future case and infection rates based at least in part on policy dates, environment clusters, and adherence and sentiment scores.

In some embodiments, step/operation 401 is configured to make predictions about the projected trend of disease growth in a target locality in response to adaptation of a particular disease control policy based at least in part on a projected social sentiment toward the particular disease control policy in the target locality and a projected adherence rate toward the particular disease control policy in the target locality. To do so, the predictive data analysis computing entity 106 may in some embodiments perform the below operations: identifying a set of related localities in which the particular disease control policy has been adopted in the past, the particular projected social sentiment toward the particular disease control policy exists, and the particular projected adherence rate toward the particular disease control policy exists; for each related locality in the set of related localities, determining a disease trend observation for each day after adaptation of the particular disease control policy; and for each day after adaptation of the particular control policy, determining a projected disease trend for the target locality based at least in part on each disease trend observation for the particular day.

The inferred cross-temporal growth prediction for an input locality data object in relation to an input control policy data object may describe an inferred prediction about growth of a target condition (e.g., an infection rate of a target disease, a hospitalization rate of a target disease, a death rate resulting from a target disease, and/or the like) across a group of temporal units (e.g., a group of days) and within the locality described by the input locality data object, where the prediction is performed by assuming that a control policy described by the input control policy data object is adopted at a temporal unit (e.g., on a day) described by a corresponding adoption timestamp of the input control policy data object. For example, the inferred cross-temporal growth prediction for an input locality data object in relation to an input control policy data object may describe, for each day of n days after an assumed adoption time of a control policy described by the input control policy data object in a locality described by an input locality data object, a per-day infection growth rate for a target disease. As another example, the inferred cross-temporal growth prediction for an input locality data object in relation to an input control policy data object may describe, for each day of n days after an assumed adoption time of a control policy described by the input control policy data object in a locality described by an input locality data object, a per-day infection rate for a target disease. As yet another example, the inferred cross-temporal growth prediction for an input locality data object in relation to an input control policy data object may describe, for each day of n days after an assumed adoption time of a control policy described by the input control policy data object in a locality described by an input locality data object, a per-day resulting death rate for a target disease. In some embodiments, the inferred cross-temporal growth prediction comprises a group of inferred temporal growth predictions, where an inferred temporal growth prediction describes an inferred prediction about growth of a target condition (e.g., an infection rate of a target disease, a hospitalization rate of a target disease, a death rate resulting from a target disease, and/or the like) at a policy-indexed temporal unit of a group of policy-indexed temporal units.

In some embodiments, step/operation 402 may be performed in accordance with the process that is depicted in FIG. 5. The process that is depicted in FIG. 5 begins at step/operation 501 when the predictive data analysis computing entity 106 generates a locality cohort for the input locality data object and the input control policy data object. The locality cohort for an input locality data object and an input control policy data object may describe a group of localities described by a group of cohort locality data objects that are deemed to have adopted the input control policy data object and where at least one of (e.g., both of) the following conditions are true of the group of cohort locality data objects: (i) each cohort locality data object is associated with a corresponding cohort locality sentiment designation with respect to the input control policy data object that corresponds to an input locality sentiment designation for the input locality data object with respect to the input control policy data object, and (ii) each cohort locality data object is associated with a corresponding cohort locality adherence designation with respect to the input control policy data object that corresponds to an input locality adherence designation for the input locality data object with respect to the input control policy data object. For example, the locality cohort for an input locality data object and an input control policy data object may describe a group of localities described by a group of cohort locality data objects that are deemed to have adopted a control policy described by the input control policy data object and where, for each particular locality of the group of localities, a recorded popular sentiment about the control policy in the particular locality corresponds to a recorded popular sentiment about the control policy in the locality described by the input locality data object, and a recorded popular adherence rate about the control policy in the particular locality corresponds to a recorded expected popular adherence rate about the control policy in the locality described by the input locality data object. In some embodiments, the input locality data object is associated with one or more input locality demographic features, each cohort locality data object of the one or more of cohort locality data objects is associated with one or more cohort locality demographic features, and each one or more cohort locality demographic features for a cohort locality data object of the one or more of cohort locality data objects corresponds to the one or more input locality demographic features.

In some embodiments, to generate the locality cohort for the input locality data object and the input control policy data object, the predictive data analysis computing entity 106 utilizes a cohort generation machine learning model. The cohort generation machine learning model may be a model that is configured to process at least one of (e.g., both of) an input locality sentiment designation for the input locality data object with respect to the input control policy data object and an input locality adherence designation for the input locality data object with respect to the input control policy data object in order to generate a locality cohort for the input locality data object and the input control policy data object that includes one or more cohort locality data objects. For example, the cohort machine learning model may be configured to perform the following operations: (i) identifying an input locality sentiment designation for an input locality data object with respect to an input control policy data object and an input locality adherence designation for the input locality data object with respect to the input control policy data object, (ii) generating a first set of locality data objects that are recorded to have adopted the input control policy data object, (iii) generating a second set of locality data objects including each locality data object in the first set of locality data objects that has a locality sentiment designation that corresponds to the input locality sentiment designation and has a locality adherence designation that corresponds to the input locality sentiment designation, and (iv) generating the locality cohort based at least in part on the set of locality data objects. In some embodiments, the cohort machine learning model is a clustering machine learning model (e.g., a k-nearest-neighbor-based clustering machine learning model), such as a clustering machine learning model that is configured to generate the locality cohort based at least in part on processing a mapping of a set of locality cohort data objects to a multi-dimensional mapping space, where the multi-dimensional mapping space is associated with a group of mapping dimensions including a mapping dimension associated with locality sentiment designations and a mapping dimension associated with locality adherence designations.

In some embodiments, step/operation 501 is performed in accordance with the process that is depicted in FIG. 6. The process that is depicted in FIG. 6 begins at step/operation 601 when the predictive data analysis computing entity 106 identifies an input locality sentiment designation for the input locality data object with respect to the input control policy data object. In general, a locality sentiment designation may describe a recorded popular sentiment toward an event (e.g., a control policy) described by a corresponding control policy data object. For example, the locality sentiment designation may describe a recorded approval rating of a corresponding control policy in a corresponding locality. In some embodiments, the locality sentiment designation for an input locality data object with respect to an input control policy data object is referred to as an input locality sentiment designation, while the locality sentiment designation for a cohort locality data object in a locality cohort with respect to an input control policy data object is referred to as a cohort locality sentiment designation.

At step/operation 602, the predictive data analysis computing entity 106 identifies an input locality adherence designation for the input locality data object with respect to the input control policy data object. In general, a locality adherence designation may describe a recorded/expected popular adherence behavior toward an event (e.g., a control policy) described by a corresponding control policy data object. For example, the locality adherence designation may describe a recorded/expected adherence rating for a corresponding control policy in a corresponding locality. In some embodiments, the locality adherence designation for an input locality data object with respect to an input control policy data object is referred to as an input locality adherence designation, while the locality adherence designation for a cohort locality data object in a locality cohort with respect to an input control policy data object is referred to as a cohort locality adherence designation.

At step/operation 603, the predictive data analysis computing entity 106 generates a first set of locality data objects that are recorded to have adopted the input control policy data object. In some embodiments, to generate the first set of locality data objects, the predictive data analysis computing entity 106: (i) identifies a set of candidate locality data objects, (ii) for each candidate locality data object of the set of locality data objects, identifies a set of adopted control policy data objects, and (iii) generates the first set of locality data objects based at least in part on a subset of the set of candidate locality data objects, where each locality data object in the subset is associated with a corresponding set of adopted control policy data objects that includes the input control policy data object.

At step/operation 604, the predictive data analysis computing entity 106 generates the locality cohort based at least in part on a subset of the first set of locality data objects, where each locality data object in the subset: (i) is associated with a locality sentiment designation with respect to the input control policy data object that corresponds to the input locality sentiment designation, and/or (ii) is associated with a locality adherence designation with respect to the input control policy data object that corresponds to the input locality adherence designation.

Returning to FIG. 5, at step/operation 502, the predictive data analysis computing entity 106 identifies (e.g., generates) a ground-truth cross-temporal growth data object for each cohort locality data object in the locality cohort. A ground-truth cross-temporal growth data object may be configured to describe a recorded property related to growth (e.g., an infection count, an infection rate, a hospitalization count, a hospitalization rate, a death count, a death rate, and/or the like) of a target disease within a corresponding locality data object during a group of policy-indexed temporal units after adoption of a corresponding control policy data object by the corresponding locality data object. In some embodiments, the ground-truth cross-temporal growth data objects includes a set of ground-truth cross-temporal growth feature values each describing a recorded property related to growth of a target disease within a corresponding locality data object during a policy-indexed temporal unit of a group of policy-indexed temporal units. For example, a ground-truth cross-temporal growth data object may describe, for each day of n days after adoption of a control policy data object by a locality data object, an infection rate of a target disease within the locality data object (where n may be defined by a hyper-parameter of the predictive data analysis system 101). A policy-indexed temporal unit may describe a unit of time (e.g., a day) that is defined based at least in part on unit-of-time separation in reference to a unit of time associated with an adaption timestamp of a control policy data object. Examples of policy-indexed temporal units include a set of policy-indexed temporal units that each corresponds to one of n days after a day associated with an adaption timestamp of a control policy data object.

At step/operation 503, the predictive data analysis computing entity 106 generates the inferred cross-temporal growth prediction for the input locality data object with respect to the input control policy data object based at least in part on each ground-truth cross-temporal growth data object for a cohort locality data object in the locality cohort. In some embodiments, to generate the inferred cross-temporal growth prediction for the input locality data object with respect to the input control policy data object, a cohort-based growth forecast machine learning model is configured to process a ground-truth cross-temporal growth data object for each cohort locality data object of the one or more cohort locality data objects with respect to the group of policy-indexed temporal units to generate the inferred cross-temporal growth prediction.

In some embodiments, the inferred cross-temporal growth prediction comprises a plurality of inferred temporal growth predictions, each inferred temporal growth prediction of the plurality of inferred temporal growth predictions is associated with a policy-indexed temporal unit of the plurality of policy-indexed temporal units, each ground-truth cross-temporal growth data object for a cohort locality data object of the one or more cohort locality data objects comprises a plurality of ground-truth temporal growth feature values, and each ground-truth temporal growth feature value of the plurality of ground-truth temporal growth feature values for a cohort locality data object of the one or more cohort locality data objects is associated with a policy-indexed temporal unit of the plurality of policy-indexed temporal units.

In some embodiments, generating the inferred cross-temporal growth prediction comprises: for each policy-indexed temporal unit of the plurality of policy-indexed temporal units, processing each ground-truth cross-temporal growth data object of the plurality of ground-truth cross-temporal predictions for a cohort locality data object of the one or more cohort locality data objects that is associated with the policy-indexed temporal unit using the cohort-based growth forecast machine learning model to generate the inferred temporal growth prediction of the plurality of inferred temporal growth predictions that is associated with the policy-indexed temporal unit; and determining the inferred cross-temporal growth prediction based at least in part on each inferred temporal growth prediction for a policy-indexed temporal unit of the plurality of policy-indexed temporal units.

In some embodiments, generating the inferred cross-temporal growth prediction comprises: (i) for each input policy-indexed temporal unit of the plurality of policy-indexed temporal units: (a) identifying a predecessor subset for the input policy-indexed temporal unit that comprises the input policy-indexed temporal unit and each policy-indexed temporal unit of the plurality of policy-indexed temporal unit that temporally precedes the input policy-indexed temporal unit, and (b) processing each ground-truth cross-temporal growth data object of the plurality of ground-truth cross-temporal predictions for a cohort locality data object of the one or more cohort locality data objects that is in the predecessor subset for the input policy-indexed temporal unit using the cohort-based growth forecast machine learning model to generate the inferred temporal growth prediction of the plurality of inferred temporal growth predictions that is associated with the input policy-indexed temporal unit; and (ii) determining the inferred cross-temporal growth prediction based at least in part on each inferred temporal growth prediction for a policy-indexed temporal unit of the plurality of policy-indexed temporal units.

As discussed above, in some embodiments, a cohort-based growth forecast machine learning model is configured to process a ground-truth cross-temporal growth data object for each cohort locality data object of the one or more cohort locality data objects with respect to the group of policy-indexed temporal units to generate the inferred cross-temporal growth prediction. The cohort-based growth forecast machine learning model may be a model that is configured to process a ground-truth cross-temporal growth data object for each cohort locality data object the one or more cohort locality data objects for an input locality data object with respect to a group of policy-indexed temporal units to generate the inferred cross-temporal growth prediction for the input control policy data object.

In some embodiments, the cohort-based growth forecast machine learning model is configured to: (i) for each policy-indexed temporal unit of a group of policy-indexed temporal units, process each ground-truth cross-temporal growth data object of the plurality of ground-truth cross-temporal predictions for a cohort locality data object of the one or more cohort locality data objects that is associated with the policy-indexed temporal unit using the cohort-based growth forecast machine learning model to generate the inferred temporal growth prediction of a group of inferred temporal growth predictions that is associated with the policy-indexed temporal unit; and (ii) determine the inferred cross-temporal growth prediction based at least in part on each inferred temporal growth prediction for a policy-indexed temporal unit of the plurality of policy-indexed temporal units.

In some embodiments, the cohort-based growth forecast machine learning model is configured to: (i) for each input policy-indexed temporal unit of a group of policy-indexed temporal units: (a) identify a predecessor subset for the input policy-indexed temporal unit that comprises the input policy-indexed temporal unit and each policy-indexed temporal unit of the plurality of policy-indexed temporal unit that temporally precedes the input policy-indexed temporal unit, and (b) process each ground-truth cross-temporal growth data object of the group of ground-truth cross-temporal predictions for a cohort locality data object of the one or more cohort locality data objects that is in the predecessor subset for the input policy-indexed temporal unit using the cohort-based growth forecast machine learning model to generate the inferred temporal growth prediction of the group of inferred temporal growth predictions that is associated with the input policy-indexed temporal unit; and (ii) determine the inferred cross-temporal growth prediction based at least in part on each inferred temporal growth prediction for a policy-indexed temporal unit of the group of policy-indexed temporal units.

In some embodiments, the cohort-based growth forecast machine learning model is a sequential processing machine learning model (e.g., a recurrent neural network machine learning model, such as a Long Short Term Memory (LSTM) machine learning model).

Returning to FIG. 4, at step/operation 403, the predictive data analysis computing entity 106 performs one or more prediction-based actions based at least in part on the inferred cross-temporal growth prediction. While various embodiments of the present invention describe performing prediction-based actions related to generating prediction output user interface data objects, a person of ordinary skill in the relevant technology will recognize other prediction-based actions (e.g., performing load balancing operations, triggering automated response mechanisms, generating one or more electronic notification alerts, and/or the like) may be performed instead of or in addition to generating prediction output user interface data objects.

In some embodiments, step/operation 403 is performed by a data visualization module that is an application (a web browser app, a mobile app, etc.) through which customers can view applicable charts and tables. In some embodiments, the data visualization module will perform two main processes: (1) display of processed data to end-users and (2) filtering information based at least in part on a default geographic unit of an end-user and/or based at least in part on manual inputs provided by the end-user. In some embodiments, display of final data to end users includes: identifying when data modeling is complete, updating visuals to new outputs of data modeling, and generating alerts to interested groups.

In some embodiments performing prediction-based actions comprises generating a prediction output user interface data object, wherein: (i) the prediction output user interface data object is configured to describe a prediction output user interface; (ii) the prediction output user interface is configured to: (a) enable updating the input locality data object from a plurality of candidate input locality data objects comprising the input locality data object and the one or more cohort locality data objects, and (b) describe a historical growth trend for the input locality data object and a projected (i.e., predicted future) growth trend for the input locality data object using a graph-based user interface element; and (iii) the projected growth trend is determined based at least in part on the inferred cross-temporal growth prediction for the input locality data object. In some embodiments, the prediction output user interface is configured to enable updating the input control policy data object. In some embodiments, the prediction output user interface is configured to enable updating the input locality sentiment designation. In some embodiments, the prediction output user interface is configured to enable updating the input locality adherence designation. In some embodiments, performing the one or more prediction-based actions further comprises providing the prediction output user interface data object to a client computing entity 102. In some embodiments, the prediction output user interface is configured to enable end-users of the client computing entity 102 to modify assumptions about particular disease control policies, about adherence rates toward particular disease control policies, and about social sentiments toward particular disease control policies.

An operational example of a prediction output user interface 700 is depicted in FIG. 7. As depicted in FIG. 7, the prediction output user interface 700 depicts a historical growth trend 701 and the projected growth trend 702 for an input locality data object 703 that is selected using the user interface segment 704, where the projected growth trend 702: (i) is determined in relation to three control policy data objects 705 and, (ii) is determined using a cohort locality that is selected based at least in part on the input locality sentiment designations 706 for the input locality data object 703 and the input locality adherence designations 707 for the input locality data object 703.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
extracting, by one or more processors and from an external data source, (1) an input locality data object, indicating a geographic area, and (2) an input control policy data object, indicating an event in the geographic area, wherein the input locality data object comprises an input locality sentiment designation and an input locality adherence designation associated with the input control policy data object;
generating, by the one or more processors and by using a cohort generation clustering machine learning model, a locality cohort, comprising a set of one or more cohort locality data objects from a plurality of cohort locality data objects, for the input locality data object and the input control policy data object by processing a mapping of the plurality of cohort locality data objects to a multi-dimensional mapping space, the multi-dimensional mapping space comprising a group of mapping dimensions that comprises a first mapping dimension associated with a plurality of locality sentiment designations and a second mapping dimension associated with a plurality of locality adherence designations, wherein a cohort locality data object of the set of one or more cohort locality data objects comprises an indication of (i) the input control policy data object, (ii) a sentiment designation that corresponds to the input locality sentiment designation, and (iii) an adherence designation that corresponds to the input locality adherence designation;
generating, by the one or more processors and by using a cohort-based growth forecast recurrent neural network machine learning model, an inferred cross-temporal growth prediction for the input locality data object with respect to the input control policy data object and in relation to a plurality of policy-indexed temporal units, wherein the cohort-based growth forecast recurrent neural network machine learning model is configured to:
(i) identify a predecessor subset for a policy-indexed temporal unit of the plurality of policy-indexed temporal units that comprises the policy-indexed temporal unit and one or more of the plurality of policy-indexed temporal units that temporally precede the policy-indexed temporal unit,
(ii) process a plurality of ground truth cross-temporal growth data objects associated with one or more of the plurality of cohort locality data objects that is in the predecessor subset to generate a plurality of inferred temporal growth predictions associated with the plurality of policy-indexed temporal units, and
(iii) determine the inferred cross-temporal growth prediction based at least in part on the plurality of inferred temporal growth predictions; and
providing, by the one or more processors and to a client computing entity, a predicted growth trend for the input locality data object using a graph-based user interface element and based at least in part on the inferred cross-temporal growth prediction.

2. The computer-implemented method of claim 1, wherein the policy-indexed temporal unit is defined in accordance with a temporal offset period with respect to an adaptation timestamp for the input control policy data object.

3. The computer-implemented method of claim 1, wherein:
the inferred cross-temporal growth prediction comprises the plurality of inferred temporal growth predictions,
an inferred temporal growth prediction of the plurality of inferred temporal growth predictions is associated with a respective policy-indexed temporal unit of the plurality of policy-indexed temporal units,
a ground-truth cross-temporal growth data object for the cohort locality data object of the set of one or more cohort locality data objects comprises a plurality of ground-truth temporal growth feature values, and
a ground-truth temporal growth feature value of the plurality of ground-truth temporal growth feature values for the cohort locality data object of the set of one or more cohort locality data objects is associated with a respective policy-indexed temporal unit of the plurality of policy-indexed temporal units.

4. The computer-implemented method of claim 3, wherein generating the inferred cross-temporal growth prediction comprises:

processing the ground-truth cross-temporal growth data object of a plurality of ground-truth cross-temporal predictions for the cohort locality data object of the set of one or more cohort locality data objects that is associated with the policy-indexed temporal unit using the cohort-based growth forecast recurrent neural network machine learning model to generate the inferred temporal growth prediction of the plurality of inferred temporal growth predictions that is associated with the policy-indexed temporal unit; and determining the inferred cross-temporal growth prediction based at least in part on the inferred temporal growth prediction for the policy-indexed temporal unit of the plurality of policy-indexed temporal units.

5. The computer-implemented method of claim 3, wherein generating the inferred cross-temporal growth prediction comprises:

identifying an input predecessor subset for an input policy-indexed temporal unit of the plurality of policy-indexed temporal units that comprises the input policy-indexed temporal unit and one or more of the plurality of policy-indexed temporal units that temporally precede the input policy-indexed temporal unit;

processing the ground-truth cross-temporal growth data object of a plurality of ground-truth cross-temporal predictions for respective cohort locality data object of the set of one or more cohort locality data objects that is in the input predecessor subset for the input policy-indexed temporal unit using the cohort-based growth forecast recurrent neural network machine learning model to generate the inferred temporal growth prediction of the plurality of inferred temporal growth predictions that is associated with the input policy-indexed temporal unit; and determining the inferred cross-temporal growth prediction based at least in part on the inferred temporal growth prediction for the input policy-indexed temporal unit of the plurality of policy-indexed temporal units.

6. The computer-implemented method of claim 1, wherein the cohort-based growth forecast recurrent neural network machine learning model comprises a sequential processing machine learning model.

7. The computer-implemented method of claim 1, wherein:

the input locality data object comprises a plurality of input locality demographic features, the cohort locality data object comprises a plurality of cohort locality demographic features, and the plurality of cohort locality demographic features for a cohort locality data object corresponds to the plurality of input locality demographic features.

8. The computer-implemented method of claim 1, further comprising:

generating a prediction output user interface data object, wherein: (i) the prediction output user interface data object is configured to describe a prediction output user interface; (ii) the prediction output user interface is configured to: (a) enable updating the input locality data object from a plurality of candidate input locality data objects comprising the input locality data object and the set of cohort locality data objects, and (b) describe a historical growth trend for the input locality data object and a projected growth trend for the input locality data object using a graph-based user interface element; and (iii) the projected growth trend is determined based at least in part on the inferred cross-temporal growth prediction for the input locality data object.

9. The computer-implemented method of claim 8, wherein the prediction output user interface is configured to enable updating the input control policy data object.

10. The computer-implemented method of claim 8, wherein the prediction output user interface is configured to enable updating the input locality sentiment designation.

11. The computer-implemented method of claim 8, wherein the prediction output user interface is configured to enable updating the input locality adherence designation.

12. A system comprising:

one or more processors; and at least one memory storing processor-executable instructions that, when collectively or independently executed by any one or more of the one or more processors, comprise causing the one or more processors to:

extract, from an external data source, (1) an input locality data object, indicating a geographic area, and (2) an input control policy data object, indicating an event in the geographic area, wherein the input locality data object comprises an input locality sentiment designation and an input locality adherence designation associated with the input control policy data object;

generate, by using a cohort generation clustering machine learning model, a locality cohort, comprising a set of one or more cohort locality data objects from a plurality of cohort locality data objects, for the input locality data object and the input control policy data object by processing a mapping of the plurality of cohort locality data objects to a multi-dimensional mapping space, the multi-dimensional mapping space comprising a group of mapping dimensions that comprises a first mapping dimension associated with a plurality of locality sentiment designations and a second mapping dimension associated with a plurality of locality adherence designations, wherein a cohort locality data object of the set of one or more cohort locality data objects comprises an indication of (i) the input control policy data object, (ii) a sentiment designation that corresponds to the input locality sentiment designation, and (iii) an adherence designation that corresponds to the input locality adherence designation;

generate, by using a cohort-based growth forecast recurrent neural network machine learning model, an inferred cross-temporal growth prediction for the input locality data object with respect to the input control policy data object and in relation to a plurality of policy-indexed temporal units, wherein the cohort-based growth forecast recurrent neural network machine learning model is configured to:

(i) identify a predecessor subset for a policy-indexed temporal unit of the plurality of policy-indexed temporal units that comprises the policy-indexed temporal unit and one or more of the plurality of policy-indexed temporal units that temporally precedes precede the policy-indexed temporal unit, (ii) process a plurality of ground truth cross-temporal growth data objects associated with one or more of the plurality of cohort locality data objects that is in the predecessor subset to generate a plurality of inferred temporal growth predictions associated with the plurality of policy-indexed temporal units, and (iii) determine the inferred cross-temporal growth prediction based at least in part on the plurality of inferred temporal growth predictions; and provide, to a client computing entity, a predicted growth trend for the input locality data object using a graph-based user interface element and based at least in part on the inferred cross-temporal growth prediction.

13. The system of claim 12, wherein:
the inferred cross-temporal growth prediction comprises the plurality of inferred temporal growth predictions,
an inferred temporal growth prediction of the plurality of inferred temporal growth predictions is associated with a respective policy-indexed temporal unit of the plurality of policy-indexed temporal units,
a ground-truth cross-temporal growth data object for the cohort locality data object of the set of one or more cohort locality data objects comprises a plurality of ground-truth temporal growth feature values, and
a ground-truth temporal growth feature value of the plurality of ground-truth temporal growth feature values for the cohort locality data object of the set of one or more cohort locality data objects is associated with a respective policy-indexed temporal unit of the plurality of policy-indexed temporal units.

14. The system of claim 13, wherein generating the inferred cross- temporal growth prediction comprises:
processing the ground-truth cross-temporal growth data object of a plurality of ground-truth cross-temporal predictions for the cohort locality data object of the set of one or more cohort locality data objects that is associated with the policy-indexed temporal unit using the cohort-based growth forecast recurrent neural network machine learning model to generate the inferred temporal growth prediction of the plurality of inferred temporal growth predictions that is associated with the policy-indexed temporal unit; and
determining the inferred cross-temporal growth prediction based at least in part on the inferred temporal growth prediction for the policy-indexed temporal unit of the plurality of policy-indexed temporal units.

15. The system of claim 13, wherein generating the inferred cross-temporal growth prediction comprises:
identifying an input predecessor subset for an input policy-indexed temporal unit of the plurality of policy-indexed temporal units that comprises the input policy-indexed temporal unit and one or more of the plurality of policy-indexed temporal units that temporally precede the input policy-indexed temporal unit;
processing the ground-truth cross-temporal growth data object of a plurality of ground-truth cross-temporal predictions for respective cohort locality data object of the set of one or more cohort locality data objects that is in the input predecessor subset for the input policy-indexed temporal unit using the cohort-based growth forecast recurrent neural network machine learning model to generate the inferred temporal growth prediction of the plurality of inferred temporal growth predictions that is associated with the input policy-indexed temporal unit; and
determining the inferred cross-temporal growth prediction based at least in part on the inferred temporal growth prediction for the input policy-indexed temporal unit of the plurality of policy-indexed temporal units.

16. The system of claim 12, wherein the one or more processors are further caused to:
generate a prediction output user interface data object, wherein: (i) the prediction output user interface data object is configured to describe a prediction output user interface; (ii) the prediction output user interface is configured to: (a) enable updating the input locality data object from a plurality of candidate input locality data objects that comprise the input locality data object and the set of one or more cohort locality data objects, and (b) describe a historical growth trend for the input locality data object and a projected growth trend for the input locality data object using the graph-based user interface element; and (iii) the projected growth trend is determined based at least in part on the inferred cross-temporal growth prediction for the input locality data object.

17. One or more non-transitory computer-readable storage media including instructions that, when executed by one or more processors, cause the one or more processors to:
extract, from an external data source, (1) an input locality data object, indicating a geographic area, and (2) an input control policy data object, indicating an event in the geographic area, wherein the input locality data object comprises an input locality sentiment designation and an input locality adherence designation associated with the input control policy data object;
generate, by using a cohort generation clustering machine learning model, a locality cohort, comprising a set of one or more cohort locality data objects from a plurality of cohort locality data objects, for the input locality data object and the input control policy data object by processing a mapping of the plurality of cohort locality data objects to a multi-dimensional mapping space, the multi-dimensional mapping space comprising a group of mapping dimensions that comprises a first mapping dimension associated with a plurality of locality sentiment designations and a second mapping dimension associated with a plurality of locality adherence designations, wherein a cohort locality data object of the set of one or more cohort locality data objects comprises an indication of (i) the input control policy data object, (ii) a sentiment designation that corresponds to the input locality sentiment designation, and (iii) an adherence designation that corresponds to the input locality adherence designation
generate, by using a cohort-based growth forecast recurrent neural network machine learning model, an inferred cross-temporal growth prediction for the input locality data object with respect to the input control policy data object and in relation to a plurality of policy-indexed temporal units, wherein the cohort-based growth forecast recurrent neural network machine learning model is configured to:
  (i) identify a predecessor subset for a policy-indexed temporal unit of the plurality of policy-indexed temporal units that comprises the policy-indexed temporal unit and one or more of the plurality of policy-indexed temporal units that temporally precedes precede the policy-indexed temporal unit,
  (ii) process a plurality of ground truth cross-temporal growth data objects associated with one or more of the plurality of cohort locality data objects that is in the predecessor subset to generate a plurality of inferred temporal growth predictions associated with the plurality of policy-indexed temporal units, and
  (iii) determine the inferred cross-temporal growth prediction based at least in part on the plurality of inferred temporal growth predictions; and
provide, to a client computing entity, a predicted growth trend for the input locality data object using a graph-based user interface element and based at least in part on the inferred cross-temporal growth prediction.

18. The one or more non-transitory computer-readable storage media of claim 17, wherein:

the inferred cross-temporal growth prediction comprises the plurality of inferred temporal growth predictions, an inferred temporal growth prediction of the plurality of inferred temporal growth predictions is associated with a respective policy-indexed temporal unit of the plurality of policy-indexed temporal units, a ground-truth cross-temporal growth data object for the cohort locality data object of the set of one or more cohort locality data objects comprises a plurality of ground-truth temporal growth feature values, and a ground-truth temporal growth feature value of the plurality of ground-truth temporal growth feature values for the cohort locality data object of the set of one or more cohort locality data objects is associated with a respective policy-indexed temporal unit of the plurality of policy-indexed temporal units.

19. The one or more non-transitory computer-readable storage media of claim 18, wherein generating the inferred cross-temporal growth prediction comprises:

processing the ground-truth cross-temporal growth data object of a plurality of ground-truth cross-temporal predictions for the cohort locality data object of the set of one or more cohort locality data objects that is associated with the policy-indexed temporal unit using the cohort-based growth forecast recurrent neural network machine learning model to generate the inferred temporal growth prediction of the plurality of inferred temporal growth predictions that is associated with the policy-indexed temporal unit; and determining the inferred cross-temporal growth prediction based at least in part on the inferred temporal growth prediction for the policy-indexed temporal unit of the plurality of policy-indexed temporal units.

20. The computer-implemented method of claim 1, wherein the cohort generation clustering machine learning model comprises a k-nearest-neighbors based clustering machine learning model.

* * * * *

UNITED STATES PATENT AND TRADEMARK OFFICE
CERTIFICATE OF CORRECTION

PATENT NO. : 12,367,399 B2
APPLICATION NO. : 17/335260
DATED : July 22, 2025
INVENTOR(S) : Alison R. Stroh et al.

Page 1 of 1

It is certified that error appears in the above-identified patent and that said Letters Patent is hereby corrected as shown below:

In the Claims

Column 29, Line 51, Claim 7, delete "for a" and insert -- for the --, therefor.
Column 29, Line 62, Claim 8, delete "comprising" and insert -- that comprise --, therefor.
Column 29, Line 63, Claim 8, delete "of cohort" and insert -- of one or more cohort --, therefor.
Column 29, Line 66, Claim 8, delete "using a" and insert -- using the --, therefor.
Column 30, Lines 57-58, Claim 12, delete "precedes precede" and insert -- precede --, therefor.
Column 31, Line 24, Claim 14, delete "cross- temporal" and insert -- cross-temporal --, therefor.
Column 32, Line 42, Claim 17, delete "designation" and insert -- designation; --, therefor.
Column 32, Lines 55-56, Claim 17, delete "precedes precede" and insert -- precede --, therefor.

Signed and Sealed this
Eleventh Day of November, 2025

John A. Squires
*Director of the United States Patent and Trademark Office*